United States Patent
Wolf et al.

(12) 
(10) Patent No.: US 6,417,365 B1
(45) Date of Patent: *Jul. 9, 2002

(54) METHOD FOR RECOVERING MEDICAMENTS FROM PREPARATIONS, AND FROM THE PRECURSORS OR WASTES THEREOF

(75) Inventors: Hans-Werner Wolf; Thomas Hille, both of Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/582,377
(22) PCT Filed: Jan. 5, 1999
(86) PCT No.: PCT/EP99/00019
§ 371 (c)(1), (2), (4) Date: Jun. 26, 2000
(87) PCT Pub. No.: WO99/34941
PCT Pub. Date: Jul. 15, 1999

(30) Foreign Application Priority Data

Jan. 7, 1998 (DE) ............ 198 00 277

(51) Int. Cl.[7] ............ C07D 471/08; B09B 3/00; C08J 11/06; A61K 9/70; C07C 217/70
(52) U.S. Cl. ............ 546/39; 540/2; 540/484; 540/576; 540/581; 540/612; 552/625
(58) Field of Search ............ 546/39; 552/625; 540/484, 2, 576, 581, 612

(56) References Cited

U.S. PATENT DOCUMENTS 5,176,916 A * 1/1993 Yamanaka ............ 424/448
5,869,652 A * 2/1999 Asmussen ............ 540/484

FOREIGN PATENT DOCUMENTS

DE 42 21 681 A1 7/1992
WO 40 37 562 C 8/1992
WO 195 24 083 A 1/1997

* cited by examiner

*Primary Examiner*—Evelyn Mei Huang
(74) *Attorney, Agent, or Firm*—Jordan and Hamburg LLP

(57) ABSTRACT

In a process for recovering medicinal substances or active substances from preparations, their initial products or waste, a flat-shaped starting material in the form of a film with adhesive and an active substance-containing material is provided with one edge length of from 0.1 to 5 cm and a second edge length of 50 cm. A starting material having an active substance is placed in an aqueous extraction liquor. The extraction liquor then takes effect until the active substance is dissolved in the aqueous extraction liquor forming an active substance-containing solution. The active substance is isolated from the active substance-containing solution be means of precipitation.

11 Claims, No Drawings

METHOD FOR RECOVERING MEDICAMENTS FROM PREPARATIONS, AND FROM THE PRECURSORS OR WASTES THEREOF

This application is the 371 of PCT/EP99/00019, filed on Jan. 5, 1999.

The present invention relates to a process for recovering medicinal substances or active substances from preparations, their initial products or waste, especially in the form of flat-shaped starting material, containing adhesively equipped film and active substance-containing material.

BACKGROUND OF THE INVENTION

The process is especially suited for active substances from unused or discarded devices for the transdermal application of active substances and/or their process waste, whereby the active substances contained in said devices are usually present in combination with polymer films and polymer sheets.

Devices for transdermal application can be subdivided into two categories:
a) systems releasing active substances to the skin or to the organism by passive diffusion, and
b) systems releasing active substances to the skin or to the organism under the action or by the aid of electric currents.

Systems based on passive diffusion are so-called transdermal therapeutic systems (TTS).

These can be further subdivided into so-called matrix systems and reservoir systems.

In matrix systems, the active substance is dissolved in polymer films or partially suspended in crystalline form or in the form of microcapsules. In the simplest case, such systems therefore consist of a backing layer which is impermeable to the active substance, an active substance-containing and preferably self-adhesive matrix, and a protective sheet to be removed prior to use.

Reservoir systems contain the active substance in a fluid reservoir. The active substance may be present in a completely or only partially dissolved form. In the simplest case, these systems consist of a backing layer impermeable to the substances contained in the reservoir and a membrane at least permeable to the active substance and preferably provided with an adhesive film for application of the system to the skin.

Systems which release the active substance to the skin or the organism under application of electric current can have various structures. They are particularly used for active substances which—owing to their chemo-physical properties—cannot penetrate the skin in a sufficient amount by means of passive diffusion.

A portion of unspent active substance remains in every worn TTS. Such active substance-containing waste products represent a toxicological or ecological risk and must therefore be disposed of as hazardous waste at extremely high expense. On the other hand, these waste products contain expensive and valuable ingredients or active substances originating from medicinal preparations, the recovery of which appears economically sensible. One reason why the economic considerations to be taken into account hereby result in favor of recovering active substances is that the carrier material, which is then substantially free of active substance, is not regarded as hazardous waste and can therefore be disposed of at a low cost.

A number of recycling methods are known from the state of the art, in particular also for recycling waste products containing adhesive-coated sheet material.

DE-OS 42 21 681 describes a method for recycling polyethylene, polypropylene or polystyrene adhesives on label waste products.

DE-OS 40 37 562 describes a recycling of adhesive-coated plastic films by repeated kneading in a solvent, drainage in a screw conveyor, and repeated passage of the remaining material in the same procedure. This publication also teaches a process for recycling plastic sheets coated with adhesive and present in shredded form by separating the plastic material and the adhesive. In a first stage, the sheet shreds are placed in a solvent for the adhesive and agitated under mechanical action for a predetermined period of time in order to disperse the adhesive adhering to the sheet shreds in the solvent. Subsequently, the adhesive dispersed in the solvent is separated from the sheet shreds under mechanical action. In a second, similar stage, fresh solvent is supplied to the sheet shreds of the first stage and the solvent-adhesive dispersion of the second stage is fed to the first stage.

DE-OS 195 24 083 describes a method for recycling TTS in which active substance is dissolved in a solvent and recovered from this solvent. However, the disclosure only states that the methods on which the invention is based are known to the person skilled in the art. In addition, this document suggests that the person skilled in the art submit the TTS to a pretreatment in order to sort out carrier and/or protective sheets, packaging material, etc.

SUMMARY OF THE INVENTION

It is the object of the present invention to provide, on this basis, a process with which it is possible to reprocess waste products of medical preparations and in particular of devices—unused or discarded after wearing—for the transdermal application of active substances, so-called TTS, in a cost-efficient manner in order to recover active substances contained therein.

DETAILED DESCRIPTION OF THE INVENTION

The method of the present invention is environmentally beneficial, economically feasible and enables the isolation of valuable raw active substances. It also results in an environmentally neutral and thus easily disposable fraction of residue of solids or carrier materials which are substantially free of active substances.

The carrier materials or residue from the process can be further recycled and disposed of according to known methods.

The process according to the invention avoids expensive process steps such as e.g. processing the materials in a pretreatment through sorting and separation into pure-grade fractions, whereby foreign materials such as carrier and/or protective sheets are sorted out and the active substance-containing material is concentrated. In the present invention, the separation is achieved by means of a complete dissolution of the active substances. An expensive size reduction of the material e.g. in a shredder, which is problematic even after embrittlement due to the pressure-sensitive adhesive characteristics, is not necessary. Rather, the dissolution and thus the prerequisite for the extraction of the active substance takes place in a liquid.

First, either an acidic extraction liquor having a pH from 1 to less than 7 or a basic extraction liquor having a pH of greater than 7 to less than 13 is added to laminates having an active substance.

Dissolution of the active substance may be intensified through additional heat treatment and/or agitation of the extraction liquor. Dissolution of the active substance may also be intensified through excitation of ultrasound in the extraction liquor.

To recover the active substance from the solution, it is advantageously provided that the recovery is carried out by precipitation.

If the active substances are extracted by means of solvents or solvent mixtures, it is advisable to use water with an acidic pH or an acidified water/alcohol mixture in the case of basic active substances and to set a basic pH value for acidic active substances. Inorganic acids or bases are particularly suitable, and especially aqueous solutions of sulfuric acid or sodium hydroxide solution with a concentration of 1%, because these substances are not volatile. The use of substantially aqueous solutions has the additional advantage that substantially lipophilic auxiliary agents are coextracted to only a small extent.

After filtering off the sheets or films, the active substances are precipitated by means of a pH shift. The thus obtained solution is filtered and the medicinal substance is purified by means of salification and/or recrystallization. The precipitation of a basic active substance can be carried out through acidification of the active-substance containing solution to a pH value of less than 6 by adding an inorganic acid.

The process is effective and economically advantageous and it achieves the object stated above in an optimum manner.

In particular the following substances can be recovered by a selection of the processing parameters: active substances with hormonal action, estradiol, estradiol derivatives, gestagens, gestagen derivatives or their mixtures, morphine or morphine derivatives, buprenorphine, physostigmine, scopolamine and galanthamine. The recovered substances can then be reused, according to their pharmaceutical action, as analgesics as well as for the treatment of senile dementia, high blood pressure, arrhythmia, vascular diseases, addictions, hyperlipidaemia, psychological disturbances, to influence blood coagulation, eating disorders, or dysglycemia.

The invention is illustrated with the help of the following examples:

EXAMPLE 1

10 m² of laminate, consisting of a siliconized polyester sheet (PET) with a thickness of 100 $\mu$m, a self-adhesive matrix containing 80 g of buprenorphine, and a PET sheet with a thickness of 23 $\mu$m is cut into strips with a width of 5 cm. These strips are cross-cut at intervals of approximately 50 cm. The resulting rectangles are stirred in sulfuric acid with a concentration of 0.1% for 60 hours. Hereby, the siliconized PET sheet becomes detached. The solution becomes cloudy because the sulfuric acid partly disintegrates the PET sheets and the matrix. After the stirring is completed, filtration is performed through a filter. The solution is brought to a pH of 8 with sodium hydroxide solution. Buprenorphine precipitates and is filtered off.

Yield: 63.2 g of buprenorphine=79% of theoretical value
Content: >98% (determined by HPLC)

EXAMPLE 2

150 buprenorphine-containing TTS from process waste (=3 g of buprenorphine) were processed as in Example 1. The TTS were extracted from the primary packaging by hand. The protective sheet, however, was not removed. Shredding did not occur.

Yield: 1.44 g of buprenorphine=48% of theoretical value

EXAMPLE 3

0.05 m² of laminate (=4 g of buprenorphine) according to Example 1 were cut into strips with a length of 5 cm and a width of 0.1 cm by hand. The processing was carried out as in Example 1. The relative yield was not higher than in Example 1. This clearly illustrates that leaving out the shredding process of the process waste is, surprisingly, of advantage.

EXAMPLE 4

1000 estradiol-containing TTS (=4 g of estradiol), unpacked but with protective sheet, are stirred in sodium hydroxide solution with a concentration of 0.1% for 72 hours. The protective sheet was a siliconized PET sheet with a thickness of 100 $\mu$m and the backing layer was a transparent PET sheet with a thickness of 15 $\mu$m which was partially detached during stirring. After completion of the stirring, the sheet rests were separated through a filter. The filtrate is brought to a pH of 1 with diluted sulfuric acid. Hereby, estradiol and terephthalic acid precipitate. They are separated from one another through absorptive precipitation with acetone.

Yield: 2.23 g of estradiol hemihydrate=50% of theoretical value

EXAMPLE 5

1000 TTS of Example 2 (=20 g of buprenorphine) and 1000 TTS of Example 4, unpacked but with protective sheet, are stirred in sodium hydroxide solution with a concentration of 0.1% for 72 hours. The sheet rests are separated through a filter. Estradiol (and terephthalic acid) are precipitated at a pH of 1. Buprenorphine is precipitated from the filtrate at a pH of 8 by adding sodium hydroxide solution. While the yield of estradiol corresponds to the value of Example 4, the yield of buprenorphine is 26%, i.e. less than in Example 2.

By means of HPLC analyses it can be shown that no mutual impurities of the two medicinal substances can be observed after recrystallization.

What is claimed is:

1. A process for the recovery of acidic or basic active substances from unused or discarded devices for the transdermal application of active substance and/or their process waste comprising the steps of:
   1) providing active substance-containing laminates having edge lengths from 5 cm by 50 cm to 5 cm. by 0.1 cm in the form of flat-shaped pieces comprising adhesive film and an active substance-containing material, said active substance-containing material comprising an active substance, said active substance being acid-soluble or base-soluble;
   2) adding to said active substance-containing laminates an acidic aqueous extraction liquor when said active substance is acid soluble or a basic aqueous extraction liquor when said active substance is base-soluble, to produce an active substance-containing solution;
   3) agitating the active substance-containing solution for a predetermined period of time in the range of 60 to 72 hours; and
   4) adding an acid to the active substance-containing solution when the active substance is base-soluble or adding a base to the active substance-containing solution when the active substance is acid-soluble to precipitate said active substance from the active substance-containing solution.

2. The process of claim 1 further comprising the step of heating the acidic aqueous extraction liquor or basic aqueous extraction liquor and/or agitating the acidic aqueous extraction liquor or the basic aqueous extraction liquor ultrasonically.

3. The process of claim 1 wherein the acidic aqueous extraction liquor comprises sulfuric acid.

4. The process of claim 1 wherein the acidic aqueous extraction liquor has a pH from 1 to less than 7.

5. The process according to claim of claim 1 wherein the basic aqueous extraction liquor has a pH from greater than 7 to 13.

6. The process of claim 1 wherein the acid added to the active substance-containing solution is an inorganic acid and the active substance-containing solution has a pH of <6.

7. The process of claim 6 wherein the inorganic acid is sulfuric acid.

8. The process of claim 1 wherein the base added to the active substance-containing solution is an inorganic base.

9. The process of claim 1 further comprising the step of filtering the active substance-containing solution prior to adding the acid or the base to the active substance-containing solution.

10. The process of claim 8 wherein the inorganic base is sodium hydroxide solution.

11. The process of claim 1 wherein the basic aqueous extraction liquor comprises sodium hydroxide.

* * * * *